United States Patent
Brignac et al.

(10) Patent No.: US 8,037,763 B2
(45) Date of Patent: Oct. 18, 2011

(54) RAIL SECTION WELD INSPECTION SCANNER

(75) Inventors: Jacques L. Brignac, Simsbury, CT (US); Robert E. Lucas, Southbury, CT (US)

(73) Assignee: ALSTOM Technology Ltd, Baden (CH)

( * ) Notice: Subject to any disclaimer, the term of this patent is extended or adjusted under 35 U.S.C. 154(b) by 304 days.

(21) Appl. No.: 12/477,395

(22) Filed: Jun. 3, 2009

(65) Prior Publication Data

US 2010/0307250 A1    Dec. 9, 2010

(51) Int. Cl.
*G01N 29/04*    (2006.01)
(52) U.S. Cl. .......................................................... 73/624
(58) Field of Classification Search .................... 73/636, 73/67.7, 71.5, 618, 624
See application file for complete search history.

(56) References Cited

U.S. PATENT DOCUMENTS

| | | | |
|---|---|---|---|
| 3,028,751 A | 4/1962 | Joy | |
| 3,552,191 A | 1/1971 | Heseding | |
| 3,960,005 A | 6/1976 | Vezina | |
| 3,962,908 A | 6/1976 | Joy | |
| 4,044,594 A * | 8/1977 | Owens et al. | 73/621 |
| 5,031,458 A | 7/1991 | Young et al. | |
| 6,748,808 B2 | 6/2004 | Lam | |
| 7,278,315 B1 * | 10/2007 | Klein et al. | 73/602 |

FOREIGN PATENT DOCUMENTS

| | | |
|---|---|---|
| JP | 09 264882 | 10/1997 |
| WO | WO 82/03920 | 11/1982 |

OTHER PUBLICATIONS

PCT International Search Report and The Written Opinion of the International Searching Authority, dated Nov. 5, 2010-(PCT/US2010/027070).
Article—"Laser-based ultrasonic rail inspection system", XP001539780, Railway Track and Structures, vol. 103, No. 10, Oct. 2007, pp. 21-23.

* cited by examiner

*Primary Examiner* — Jewel V Thompson
(74) *Attorney, Agent, or Firm* — Lawrence P. Zale

(57) ABSTRACT

A rail section weld inspection device [1000] is described for inspecting a rail [10] for internal defects [19,21]. A central ultrasonic (US) probe [1330] transmits at least one US beam [B] through the rail [10] and receiving a reflected signal. At least one angled US probe [1310] transmits at least one US beam [A1-A5] through the rail [10] at an oblique angle at least partially covering the same region as the central probe [1330]. An encoder identifies the location of the US probes [1330] and [1310] along the rail [10] and pairs the locations of the probes with the signals received. The Calculation device [1500] receives the signals from the US probes and uses their different views to create an image of the flaws within the rail [10].

19 Claims, 7 Drawing Sheets

RAIL SECTION WELD INSPECTION SCANNER

TECHNICAL FIELD

The present disclosure relates to a system for accurately inspecting a rail weld for weld defects, and more specifically a system for employing ultrasound to accurately inspect a rail weld for weld defects.

BACKGROUND

As sections of railroad are constructed it is necessary to weld one rail to the adjacent rail. The rails are welded end-to-end by a process called thermetic welding. In this process, the rails are placed in the desired positions. A material designed to burn at high temperature is wrapped around the rail joint and ignited. It burns at a high temperature and welds the rails together their entire cross-section.

This process sometimes creates bubbles or other flaws that lead to a weakening of the joint. It is necessary to identify these flaws so that the joint be replaced with a stronger joint without weld flaws.

Rails and weld also deteriorate with time and use. Therefore there is also a need to inspect rails and welds for flaws created by extended service & fatigue.

Since there is a large amount of weight carried by the rails, flaws may cause weakened sections and result in a derailment.

There are ultrasonic inspection devices to inspect welds in specific geometries such as sheets and plates, such as U.S. Pat. No. 3,552,191 Jan. 5, 1971 by Heseding. This uses multiple ultrasound (US) transmitters that are also US receivers on one side of a weld on a sheet or plate. They also have embodiments that transmit across the weld to be received by a receiver on the other side of the weld. This apparatus is designed to inspect welds in flat plates and does not function well to inspect objects with substantially different geometry such as railroad rails.

U.S. Pat. No. 3,028,751 issued Apr. 10, 1962 to I. L. Joy describes a device designed to quickly detect locations that may possibly have flaws. It does not perform a thorough scan through the rail, but a more cursory scan to detect a general region have a large flaw.

Currently, there is a need for an inspection device that more accurately identifies flaws in railroad rail thermite welds.

SUMMARY

The present invention may be embodied as a rail weld inspection device
for inspecting internal volumes of an elongated object [10] for defects, the elongated object 10 extending in a horizontal "z" direction with a vertical direction being a "y" direction and a direction perpendicular to both the "y" and "z" directions, being the "x" direction and for providing the information to a calculation device [1500], comprising:
a central ultrasonic (US) probe [1330] for transmitting at least one US beam [B] through said elongated object [10], for receiving a reflected signal, and for providing the signal to said imaging device;
at least one angled US probe [1310] for transmitting at least one US beam [A1-A5] through the elongated object [10] at an oblique angle within an y, z, plane which intersects with the beam B from the central US probe [1330], and adapted to receive reflected signals from the same oblique angle, and for providing the signal to said imaging device;
an encoder [1380] adapted to identify a location of the US probes [1330] and
along the elongated object [10] as the reflected signals are received and for pairing the locations of the probes corresponding to the received signals and for providing this information to the imaging device to create a map of flaws within the elongated object [10].

The central US probe 1330 may transmit a plurality of parallel US beams [B1-B5] generally in the "y" direction.

The central US probe [1330] may also transmit a plurality of US beams [D1-D10] obliquely in an "x, y" plane.

Also, the angled US probes [1310,1350] may transmit beams [A1-A5], [C1-C5] at a plurality of angles and receive each reflected signal independently from the same angle as each had been transmitted.

OBJECTS OF THE INVENTION

It is an object of the present invention to provide an accurate weld inspection system for railroad rails.

It is another object of the present invention to provide an accurate weld inspection system that accurately inspects rail welds without having to remove the rails.

It is another object of the present invention to provide an accurate weld inspection system that is portable.

It is another object of the present invention to provide a thorough inspection through a rail weld and identify flaws within the weld.

It is another object of the present invention to scan through a volume of a welded rail at various angles to identify flaws within the weld.

BRIEF DESCRIPTION OF THE DRAWINGS

Referring now to the drawings, wherein like items are numbered alike in the various Figures.

DETAILED DESCRIPTION

Theory

Figure 1:
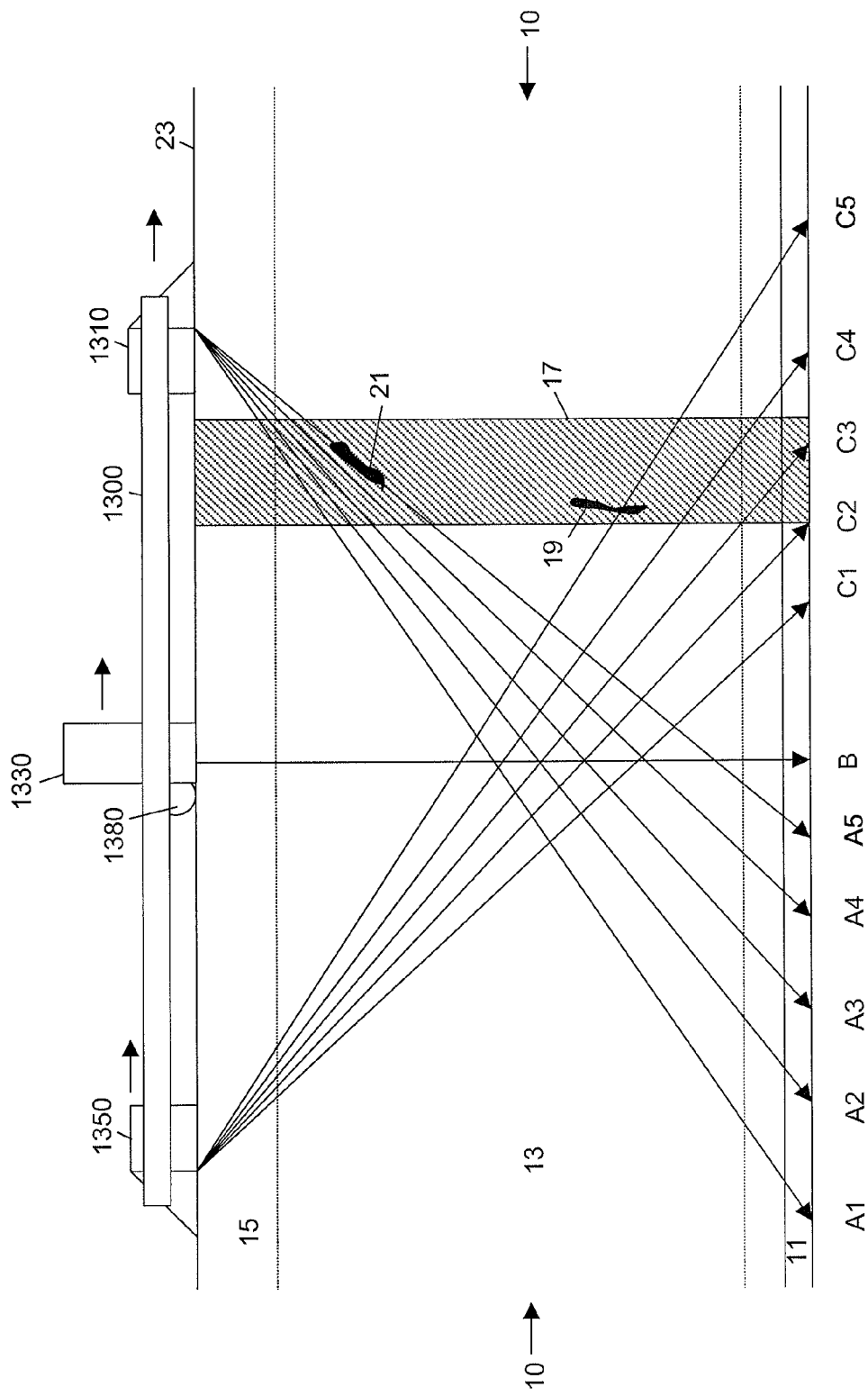
FIG. 1 is a schematic illustration of the ultrasound beams scanning through a railroad rail weld according to one embodiment of the present invention.

When inspecting at a flaw from a given viewing angle, it is sometimes hard to detect the flaw. This may be due to the fact that the flaw has a very small cross section when viewed from a given viewing angle. The same flaw viewed from another angle has a much larger cross section and is easier to detect and view.

Therefore, proper inspection through a volume is not only dependent upon the portions of an object scanned, but also on the angle from which the inspection is performed.

Commonly inspection is performed using ultrasound. Typically, an ultrasound (US) transceiver is used having both an US transmitter and an US receiver. In the present invention, the ultrasound is transmitted as a beam at various angles. The US beam reflects off of metal air interfaces and is received by the transceiver. Therefore, one may locate a flaw by knowing the angle of the transmitted beam, the shape and geometry of the material through which it is transmitted (to determine reflective interfaces) and the time at which a reflected US beam (an "echo") is received from the transmitted direction.

Some transmitters, transmit in a given direction, and move to a new direction and transmit in that direction. Echoes (if any) are detected from each of the transmitted directions, and the times of reception stored. Therefore, a volume may be sequentially scanned over a time period. If the transducer is moved during the scanning process, a number of echoes are received at various locations and angles. This may result in locations being missed.

The transducers may also transmit several beams at different angles simultaneously, and receive the reflected echoes at different various receive angles. The time delays indicate the location along the beam path of where a reflecting object (flaw) is located.

Also, due to the shape of the transmitted beams and the geometry of the object being inspected, it may not be possible to reach certain volumes of the object being inspected.

Therefore, for thorough inspection of an object by ultrasound, one must take into account the shape of the beam used, the placement of the transducer or transducers, the location of the transducers relative to the object, and the geometry of the object being scanned and other factors.

The present invention addresses all of these issues. It employs several transmitter/detectors modules. Each transducer module has a plurality of transducers each transmitting and receiving at different angles. Therefore, a full set of data is received at each instant allowing the device as it is moved relative to the object.

The multiple transducer modules are angled to converge on a central location. Therefore, multiple views from the multiple modules are simultaneously provided for the central location.

Therefore, a flaw may be inspected by several transducers from different angles at the same time. These signals may be used to provide a composite view. Since there is some redundancy in the data, the redundancy may be used to eliminate imaging artifacts. The redundancy may also be used to corroborate the existence of a flaw and more accurately delineate the bounds of the flaw.

One intended use of the present invention is for inspecting welds in railroad rails for flaws. A railroad rail has the base, vertical wall and the runner sections. The left-right dimension is the "x" axis, with the up-down direction being the "y" axis. The "z" axis is taken along the length of the rail.

Therefore, the weld is generally a thin volume between the rails in the x-y plane with a small thickness in the z direction.

There is only access to the top and sides of the rail. Therefore, any inspection must take place from these locations. The thermetic weld extends outward from the rail to both side and the top. The top section is ground down to make it smooth with the top of the rail. This allows the train wheels to smoothly roll over the top surface of the rail. This also allows the present invention to slide easily over the top surface of the rail. The sides are typically not ground down and provide obstructions to sliding along the sides. Therefore, the present invention should slide along the top surface of the rail, images from the top of the rail, have multiple transducers which provide multiple simultaneous views of volume, encode its location with the signals, and cover the volumes of interest within the rail.

FIG. 1 shows a schematic diagram illustrating the inspection geometry of a railroad rail 10 being inspected. This rail 10 has been welded leaving a weld section 17. There are two flaws 19, 21 inside of weld section 17. These may have been created during the welding process or have been created over time as deterioration of the rail 10 or weld section 17.

In this embodiment, there are three probes, a front probe 1150, a center probe 1130 and a rear probe 1150. The front probe 1110 transmits a plurality of US beams at different angles into rail 10. For the sake of clarity, only five beams are represented here labeled A1, A2, A3, A4, A5. Beam A5 impinges upon and is reflected back by flaw 21. This is detected as an echo by front probe 1110. Flaw 21 has a small cross-section as viewed from front probe 1110. It is small enough so that the other beams A1-A4 do not impinge upon it, and the image is difficult to discern with the information from a single reflected beam.

Similarly, the rear probe 1150 transmits a plurality of US beams at different angles into rail 10. For the sake of clarity, only five are represented here labeled C1, C2, C3, C4, C5. These US beams do not intersect either flaw 19 or 21 and are not reflected.

The center probe 1130 rests upon a top surface 23 of rail 10 and transmits a plurality of parallel US beams into rail 10. In this view they are stacked behind each other. Therefore they may all be represented by B1. These pass through the rail top section 15, the vertical wall 13 and the rail base 11. These US beams also do not intersect either flaw 19 or 21 and are not reflected.

The probes are attached to a runner 1300 that is allowed to move probes 1110, 1130, 1150 in the direction of the arrows relative to the rail 10. Runner 1300 includes a position encoder and wheels. Therefore, the position of the runner is known as it moves.

Figure 2:
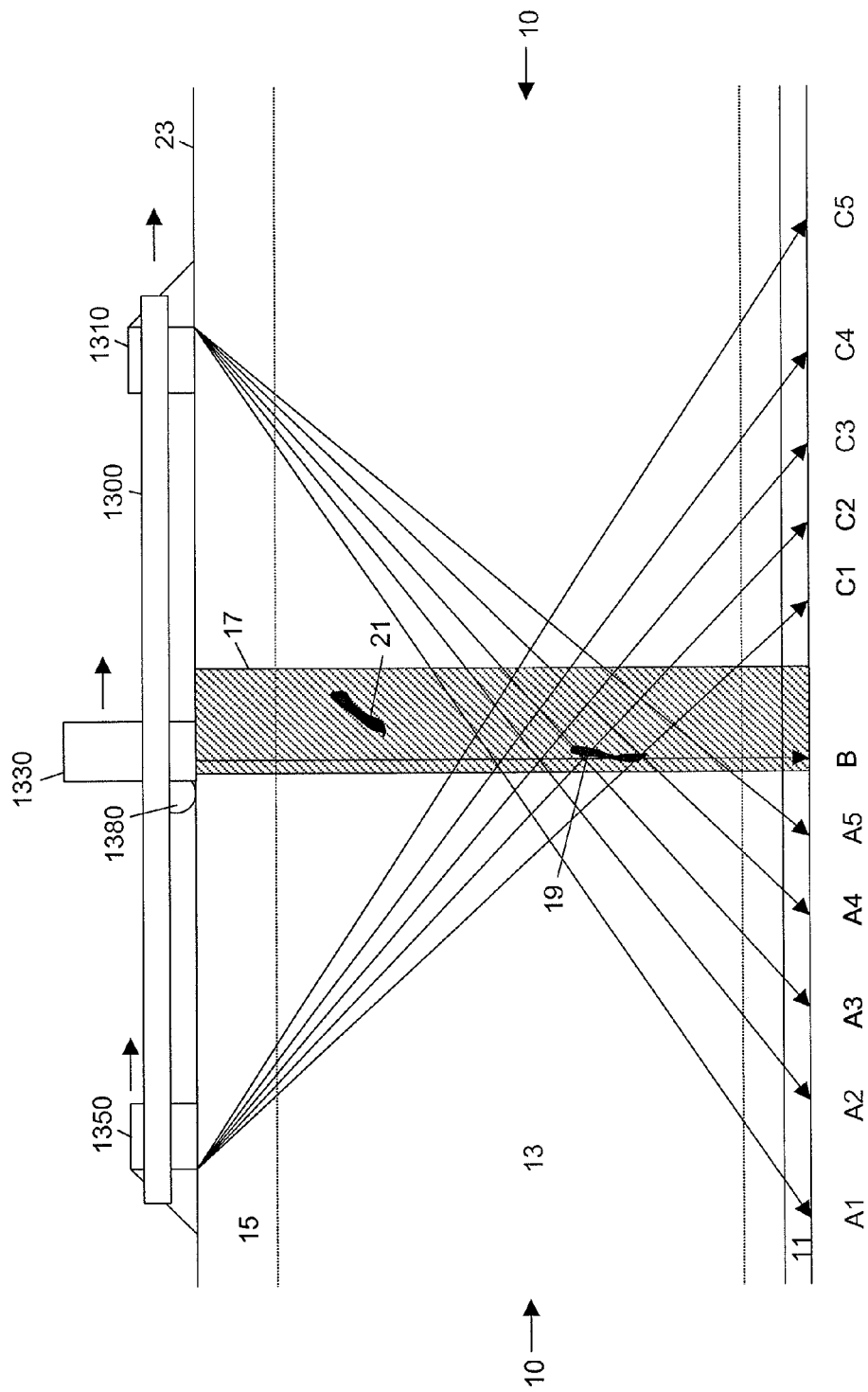
FIG. 2 is a schematic illustration of the ultrasound beams of the embodiment of FIG. 1 wherein the beams have been moved relative to the weld.

FIG. 2 shows a schematic diagram illustrating the probes of FIG. 1 inspecting the railroad rail 10 at near the weld section. In this figure, center probe 1130 is now positioned above weld section 17. Now beams B of center probe 1130 are reflected by flaw 19.

Beams C1, C2 of rear probe 1150 are reflected by flaw 19. Similarly beams A2 and A3 of front probe 1110 are reflected by flaw 19. None of the beams from front or rear probes 1110, 1150 impinge upon flaw 21 in this position.

Each transducer in the probes is capable of determining when a beam was transmitted and when a corresponding signal (echo) is received.

The reflected signals from the probes are sent to a processing unit along with an identification of the angle in which the beam was transmitted and where the probe was located during the transmission in relation to the rail being inspected. The elapsed time between transmission and reception of each echo is determined and this, along with the other transmitted information is used to reconstruct an image of the rail 10 and flaws 19, 21. Since multiple signals may be used to indicate a singe flaw, the redundancy may be used to eliminate artifacts and further specify the bounds of the flaw. As is shown in FIG. 2, flaw 19 is better seen from the front and rear probes 1110, 1150 as compared with center probe 1130. Center probe 1130 only sees a small cross section, whereas probes 1150 and 1110 see a larger side of the flaw 19.

Similarly, flaw 21 has a very small cross section when viewed by front probe 1110 since it lines up with the beams and allows only its small cross section to be visible.

Figure 3:
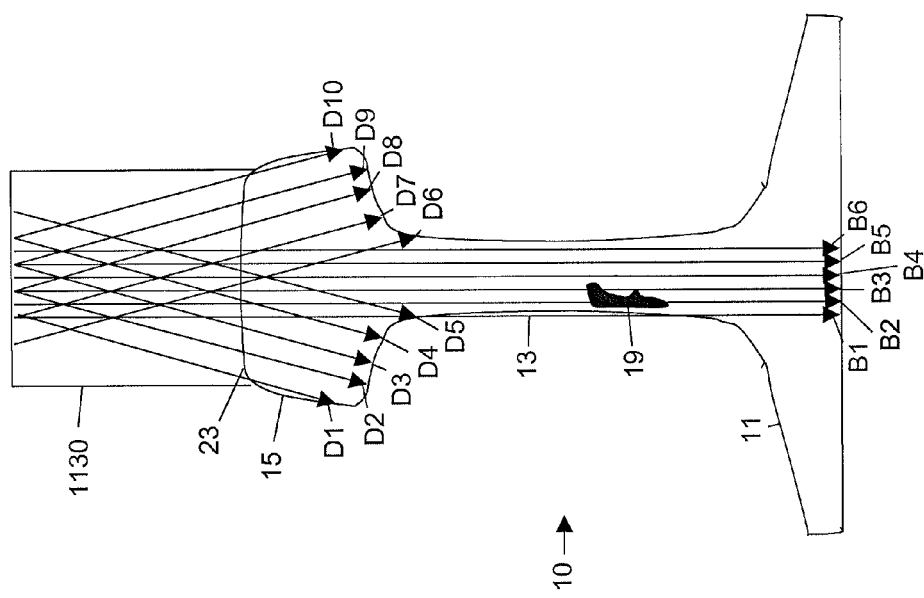
FIG. 3 is an illustration of the US beam geometry of the central probe of one embodiment of the present invention.

FIG. 3 is an illustration of the US beam geometry of the central probe of one embodiment of the present invention. From this view, only flaw 19 can be seen. This shows cross-sectional shape that is viewed from 90 degrees away from the view of FIGS. 1, 2. The cross section of a railroad rail 10 can be seen.

Here a cross section of rail 10 through the weld 17 can be seen. The base 11 that is fixed to a structure to hold the rail 10. The vertical wall 13 has a flaw 19 inside of it.

Central probe 1130 is designed to function to scan through the rail 10. As stated above, it functions to provide parallel US beams through the vertical wall 13 a base 11. This would detect flaw 19.

It may also produce a set of beams D1, D2, D3, D4, D5 angled through one side of the top portion 15. It may also produce a set of beams D6, D7, D8, D9, D10 angled through the other side of top portion 15. This creates a thorough inspection of the entire top section 15, vertical wall and a critical portion of the base 11.

Figure 4:
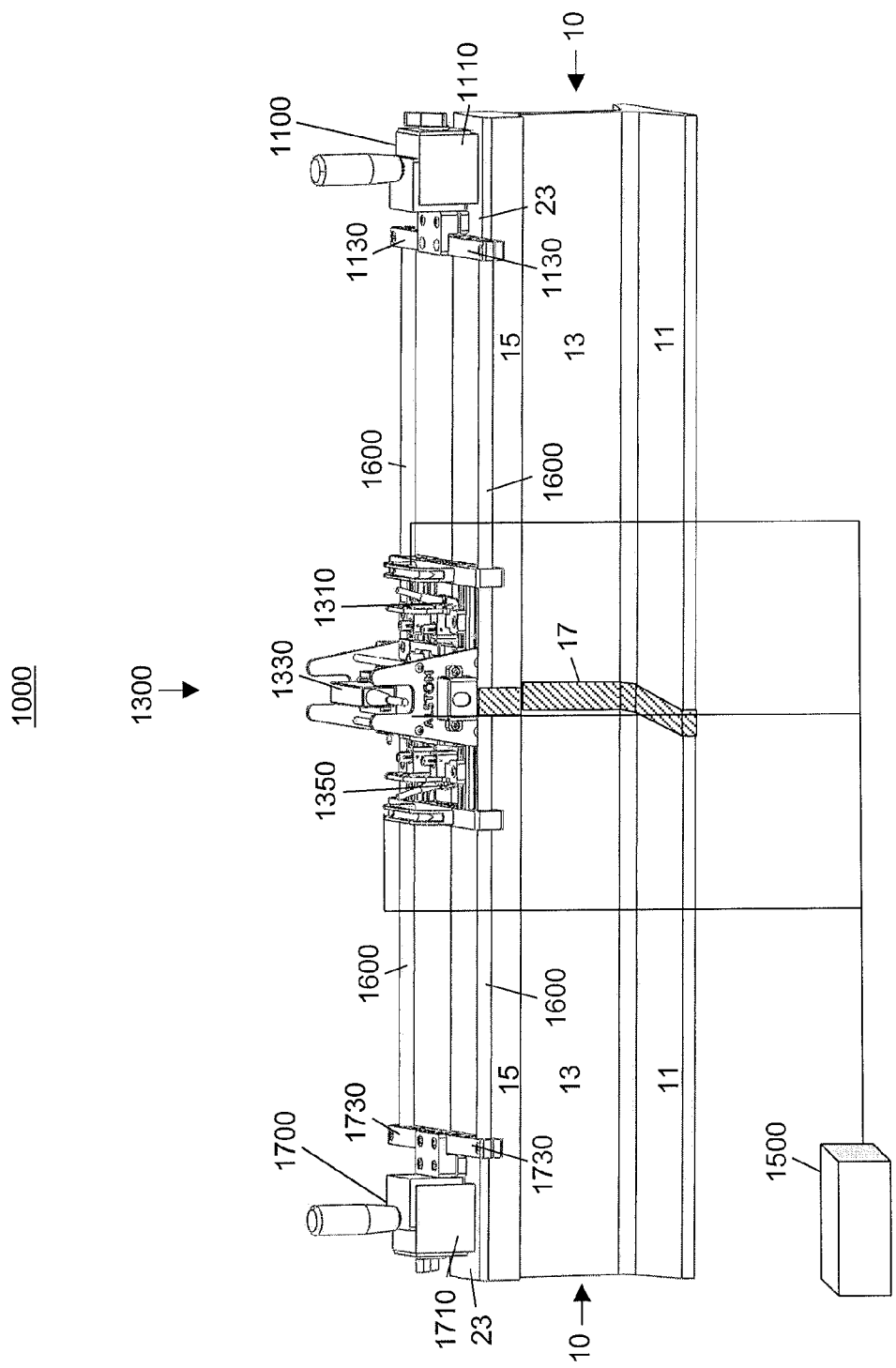
FIG. 4 is a perspective view of the weld inspection system according to one embodiment of the present invention.

FIG. 4 is a perspective view of the weld inspection system according to one embodiment of the present invention. Here two rails 10 are shown welded together with a thermetic weld at weld section 17. Rail 10 and weld section 17 are intended to be inspected for flaws by rail inspection device 1000.

End structures 1100, 1700 are removeably attached to rails 10. This may be through the use of magnets as front attachment unit 1110 and rear attachment unit 1710. Other attachment means may also be implemented.

A plurality of rod supports 1130, 1730 hold rods 1600 substantially parallel to rails 10.

A runner 1300 is slidingly attached to rods 1600 and is allowed to move along the length of rails 10 by sliding on rods 1600.

An encoder (not shown) is used to identify where the runner is with respect to rails 10.

In this embodiment, runner 1300 includes three ultrasound ("US") transmitter/receivers, a front probe 1310, a central probe 1330 and a rear probe 1350.

Both the front probe 1310 and the rear probe 1350 transmit US beams at an angle to a location within the rails 10 below central probe 1350. They also receive reflected US signals from the same direction. This is more clearly seen in FIGS. 1 and 2 where beams "A1-A5" of the front probe 1110 and beams C1-C5 of the rear probe 1150 intersect beam "B" of the central probe 1130. This provides simultaneous imaging of a location by more than one beam and from more than one direction.

The signals acquired by the front probe 1310, central probe 1330 and rear probe 1350 are send to a calculation device 1500. Calculation device 1500 identifies the location of the flaws from the signals provided to it. It may also reconstruct an image of the flaws and perform other characterizations of the flaws.

Calculation device 1500 also has the ability to store information for later comparison. Therefore, prior stored signals may be compared with newer signals to determine changes of the flaw over time. This may be important for identifying crack growth.

Calculation device 1500 may employ known reconstruction, or new algorithms to perform these functions.

Figure 5:
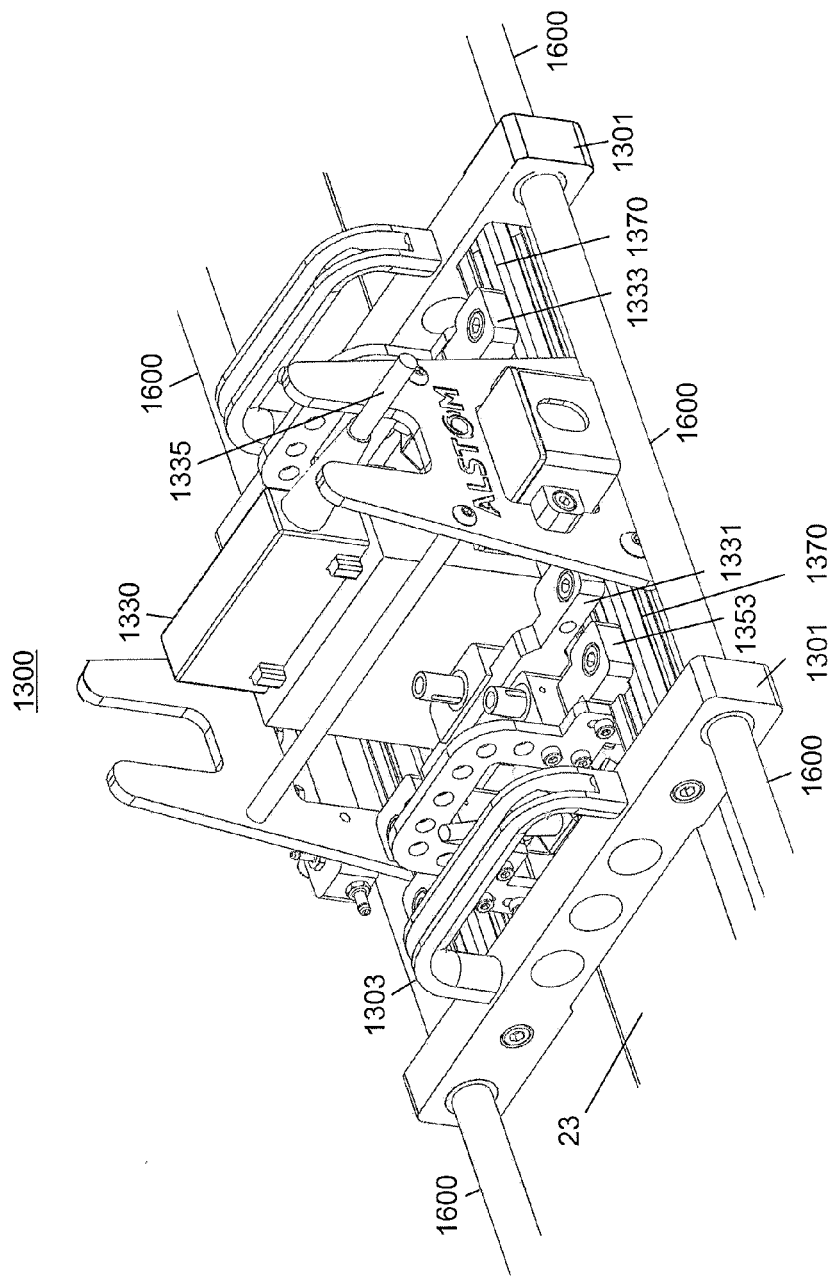
FIG. 5 is an enlarged perspective view of the runner of the weld inspection system according to one embodiment of the present invention.

FIG. 5 is an enlarged perspective view of the runner 1300 of the weld inspection system 1000 according to one embodiment of the present invention.

Figure 6:
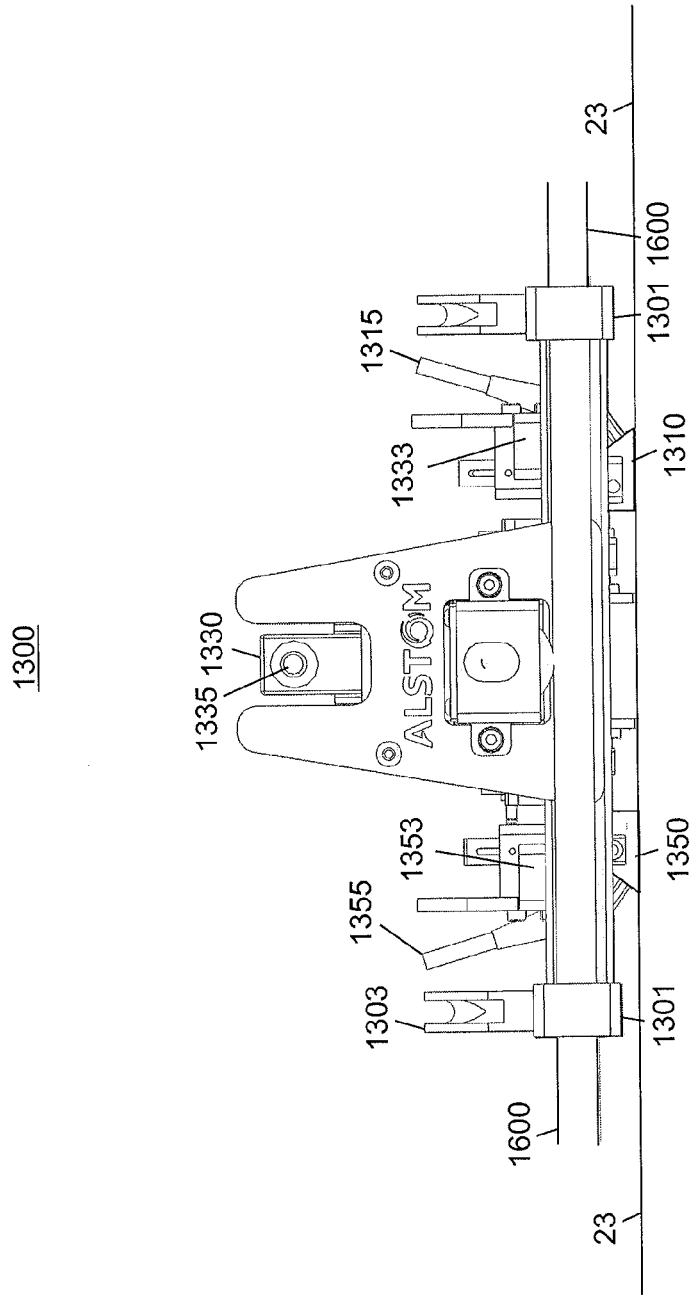
FIG. 6 is a side elevational view of the runner of the weld inspection system shown in FIGS. 4 and 5.

FIG. 6 is a side elevational view of the runner of the weld inspection system shown in FIGS. 4 and 5.

Figure 7:
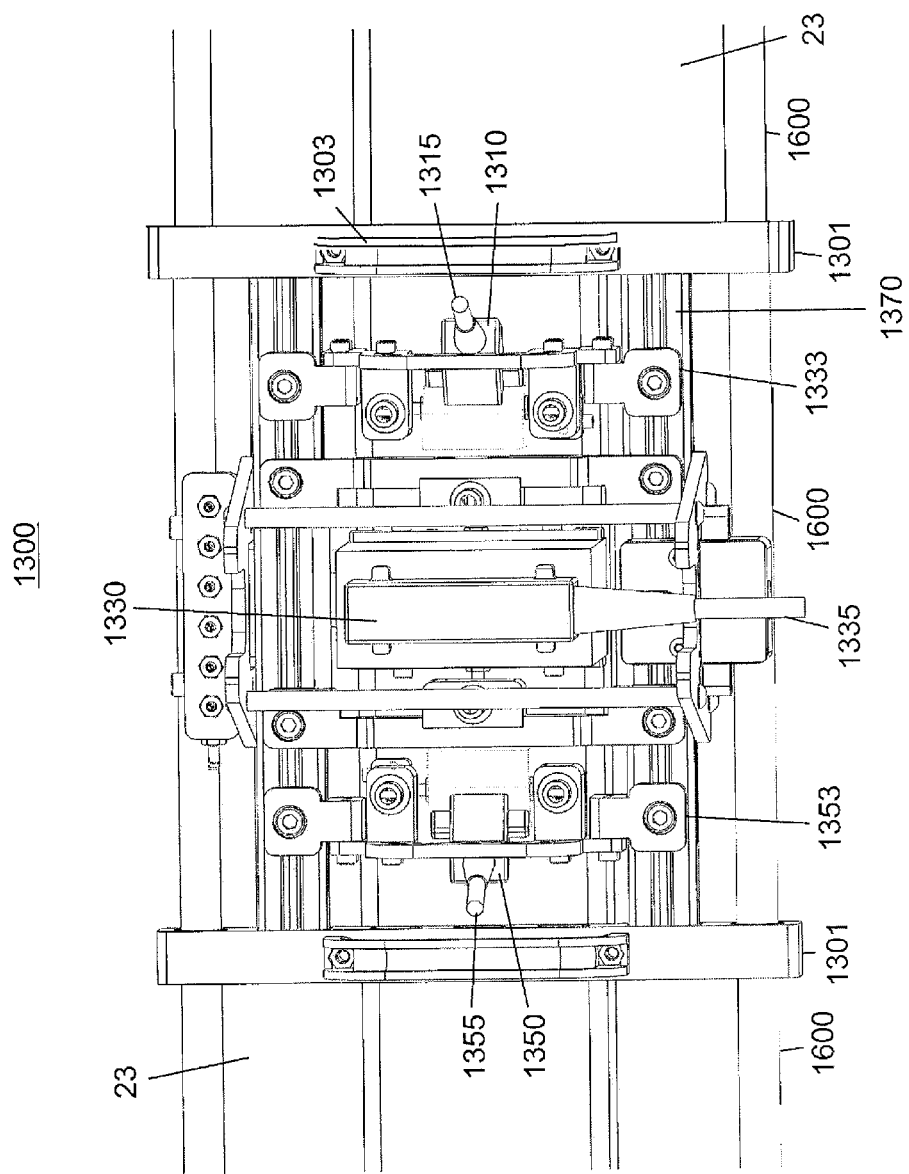
FIG. 7 is a top plan view of the runner of the weld inspection system shown in FIGS. 4, 5 and 6.

FIG. 7 is a top plan view of the runner of the weld inspection system shown in FIGS. 4, 5 and 6.

The embodiment of the present invention will now be described with reference to FIGS. 5-7.

The runner 1300 has sliders 1301 that slide along rods 1600. Rods 1600 are held by rod supports 1130, 1730. A user positions the runner 1300 by moving one or more handles 1303 attached to runner 1300.

A front probe support 1333 secures the front probe 1310 to abase 1370. The base 1370 may be an elongated plate, or other anchoring structure attached to runner 1300. A rear probe support 1353 secures the rear probe 1310 to the base 1370.

Central probe 1330 is held in place at its lower end by central probe base support 1331. It is also held in place by central probe side supports 1333.

The present invention functions by moving the runner 1300 with the probes 1110, 1130, 1150 are relative to the rail 10 keeping the same convergent view of a central location such that the central location corresponds to a different volume within rail 10 as the probes are moved to a new location. This allows the probes to scan through rail 10 as they are moved relative to the rail 10. The signals from the front probe 1310, the central probe 1330 and the rear probe 1350 are passed through cables 1315, 1335, 1355 to calculation device (1500 of FIG. 4).

The encoder (1380 of FIGS. 1, 2) also provides to the calculation unit an encoded location along rail 10 where each probe was located when a signal was received along with the corresponding signals. Therefore, for each instant of a received signal is paired with a location at which the signal was received. This allows the calculation device 1500 to create use conventional methods to create a map of the flaws.

Redundant data from other probes is used to eliminate noise and rule out false positives. They may also be used to create multi dimensional models of the flaws.

The present invention has been described in connection with the embodiment shown in the figures for illustration purposes. It is understood the present invention also covers devices having more or fewer transducers, and which may be positioned at different angles relative to each other.

In an alternative embodiment, the runner 1300 may also have a motor that moves it and the probes along the rail 10.

Although the invention has been described and illustrated with respect to exemplary embodiments thereof, it should be understood by those skilled in the art that the foregoing and various other changes, omissions and additions may be made therein and thereto, without parting from the spirit and scope of the present invention. Accordingly, other embodiments are within the scope of the following claims.

What is claimed is:

1. A rail inspection device [1000] for inspecting internal volumes of an elongated object [10] for defects, the elongated object 10 extending in a horizontal "z" direction with a vertical direction being a "y" direction and a direction perpendicular to both the "y" and "z" directions, being the "x" direction and for providing the information to a calculation device [1500], comprising:

a central ultrasonic (US) probe [1330] for transmitting at least one US beam [B] through said elongated object [10], for receiving a reflected signal, and for providing the signal to said calculation device [1500];

at least one angled US probe [1310] for transmitting at least one US beam [A1-A5] through the elongated object [10] at an oblique angle within an y, z, plane which intersects with the beam [B] from the central US probe [1330], and adapted to receive reflected signals from the same oblique angle, and for providing the signal to said calculation device [1500];

an encoder [1380] adapted to identify a location of the US probes [1330] and [1310] along the elongated object [10] as the reflected signals are received and for pairing the locations of the probes corresponding to the received signals and for providing this information to the calculation device [1500] to identify locations of the defects [19,21] within the elongated object [10].

2. The rail weld inspection device [1000] of claim 1, further comprising:
a first attachment structure [1100] removeably attached to said elongated object [10];
a second attachment structure [1700] removeably attached to said elongated object [10];
at least one rod [1600] secured between the attachment structures [1100,1700] running substantially parallel to the elongated object [10];
a runner [1300] for holding the probes in a known position relative to each other, the runner [1300] slidingly attached to the rods [1600] allowed to move along the elongated object [10].

3. The rail weld inspection device [1000] of claim 1, wherein the elongated object [10] is a standard railroad rail [10].

4. The rail weld inspection device [1000] of claim 1, wherein the central US probe 1330 transmits a plurality of parallel US beams [B1-B5] generally in the "y" direction.

5. The rail weld inspection device [1000] of claim 1, wherein the central US probe [1330] transmits a plurality of US beams [D1-D 10] obliquely in an "x, y" plane.

6. The rail weld inspection device [1000] of claim 3 wherein the central US probe [1330] transmits a plurality of parallel US beams [D1-D10] obliquely covering the majority of a top section [15] of rail [10].

7. The rail weld inspection device [1000] of claim 1, wherein the central US probe [1330] transmits a plurality of parallel US beams [B1-B5], [D1-D10].

8. The rail weld inspection device [1000] of claim 1, wherein the angled US probes [1310,1350] transmit beams [A1-A5], [C1-C5] at a plurality of angles and receives each reflected signal independently from the same angle as each had been transmitted.

9. A rail inspection device [1000] for inspecting internal volumes of a rail [10] for defects [19,21], comprising:
a first attachment structure [1100] removeably attached to said rail [10];
a second attachment structure [1700] removeably attached to said rail [10];
at least one rod [1600] secured between the attachment structures [1100,1700] running substantially parallel to the rail [10];
a runner 1300 slidingly attached to the rods [1600] allowed to move along the rail [10];
an encoder [1380] adapted to identify a location along the rail [10];
a central ultrasonic probe [1330] for transmitting at least one ultrasonic (US) beam [B] substantially vertically through said rail [10], and for receiving a reflected signal;
at least one angled ultrasonic probe [1310] for transmitting at least one US beam [A1-A5] through the rail 10 at an oblique angle which intersects with the beam [B] from the central US probe [1330], and adapted to receive reflected US signals received from the same oblique angle;

the device [1000] further adapted to provide the identified locations along the rail 10 paired with any reflected signals received at the identified locations to a calculation device [150] that is adapted to identify locations of defects [19,21] within the rail.

10. The rail inspection device [1000] of claim 9, wherein the at least one attachment structure [1100,1700] comprises:
a magnetic structure which removeably connects to said rail [10].

11. The rail inspection device 1000 of claim 9, wherein front US probe 1310 is in contact with a top surface [23] of rail [10].

12. The rail inspection device 1000 of claim 9, wherein central US probe [1330] is in contact with a top surface [23] of rail [10].

13. The rail inspection device 1000 of claim 9, wherein rear US probe [1350] is in contact with a top surface [23] of rail [10].

14. The rail inspection device 1000 of claim 9, wherein the object [10] being inspected is a conventional railroad rail [10].

15. The rail inspection device 1000 of claim 9, further comprising: a second angled US probe 1350 for transmitting at least one US beam [C1-C5] through the rail [10] at an oblique angle which intersects with the beam B from the central US probe [1330].

16. A rail inspection device [1000] for inspecting internal volumes of an elongated object [10] for defects, the elongated object 10 extending in a horizontal "z" direction with a vertical direction being a "y" direction and a direction perpendicular to both the "y" and "z" directions, being the "x" direction and for providing images of said defects, comprising: a calculation device [1500] adapted to create images of objects from US signals provided to it;
a central ultrasonic (US) probe [1330] for transmitting at least one US beam [B] through said elongated object [10], for receiving a reflected signal, and for providing the signal to the calculation device [1500];
at least one angled US probe [1310] for transmitting at least one US beam [A1-A5] through the elongated object [10] at an oblique angle within an y, z, plane which intersects with the beam B from the central US probe [1330], and adapted to receive reflected signals from the same oblique angle, and for providing the signal to said calculation device [1500] device;
an encoder [1380] adapted to identify a location of the US probes [1330] and [1310] along the elongated object [10] as the reflected signals are received and for pairing the locations of the probes corresponding to the received signals and for providing this information to the calculation device [1500] that an image of flaws within the elongated object [10].

17. The rail weld inspection device [1000] of claim 16, wherein the central US probe 1330 transmits a plurality of parallel US beams [B1-B5] generally in the "y" direction.

18. The rail weld inspection device [1000] of claim 16, wherein the central US probe [1330] transmits a plurality of US beams [D1-D10] obliquely in an "x, y" plane.

19. The rail weld inspection device [1000] of claim 16, wherein the angled US probes [1310,1350] transmit beams [A1-A5], [C1-C5] at a plurality of angles and receives each reflected signal independently from the same angle as each had been transmitted.

* * * * *

UNITED STATES PATENT AND TRADEMARK OFFICE
CERTIFICATE OF CORRECTION

PATENT NO.         : 8,037,763 B2
APPLICATION NO.    : 12/477395
DATED              : October 18, 2011
INVENTOR(S)        : Jacques L. Brignac and Robert E. Lucas It is certified that error appears in the above-identified patent and that said Letters Patent is hereby corrected as shown below:

Column 4, line 11, claim reference numeral "1150", the first occurrence, should read --1310--;
Column 4, line 11, claim reference numeral "1130" should read --1330--;
Column 4, line 11, claim reference numeral "1150", the second occurrence, should read --1350--;
Column 4, line 12, claim reference numeral "1110" should read --1310--;
Column 4, lines 17 and 18, for the claim reference numeral "1110", each occurrence, should read --1310--;
Column 4, line 22, claim reference numeral "1150" should read --1350--;
Column 4, line 24, after the sentence ending with "...C5" insert new sentence --Beam C5 intersects flaw 19.--;
Column 4, lines 25 and 26, cancel text "either", "19 or", and "and are not reflected";
Column 4, line 27, claim reference numeral "1130" should read --1330--;
Column 4, line 35, cancel text "1110, 1130, 1150" and insert text --1310, 1330, 1350--;
Column 4, line 37, after the sentence ending with the text "wheels", insert --1380--;
Column 4, lines 41 and 42, claim reference numeral "1130", each occurrence, should read --1330--;
Column 4, line 44, claim reference numeral "1150" should read --1350--;
Column 4, lines 45, 46, and 61, claim reference numeral "1110", each occurrence, should read --1310--;
Column 4, lines 47 and 62, claim reference numeral "1150" should read --1350--;
Column 4, line 62, claim reference numeral "1130", each occurrence, should read --1330--;
Column 4, line 63, claim reference numeral "1150" should read --1310--;
Column 4, line 64, claim reference numeral "1110" should read --1350--;
Column 4, line 66, claim reference numeral "1110" should read --1310--,
Column 5, line 10, claim reference numeral "1130" should read --1330--;
Column 5, line 26, cancel text "be through the use of" and insert text --includes--;
Column 5, line 43, claim reference numeral "1110" should read --1310--;
Column 6, line 10, claim reference numeral "1310" should read --1350--;
Column 6, line 16, cancel text "1110, 1130, 1150" and insert text --1310, 1330, 1350--;
Column 7, lines 10, 15 and 45, claim reference numeral "1100", each occurrence, should read --1110--;

Signed and Sealed this
Seventh Day of February, 2012

David J. Kappos
*Director of the United States Patent and Trademark Office*

CERTIFICATE OF CORRECTION (continued)
U.S. Pat. No. 8,037,763 B2

Column 7, lines 12, 15 and 46, claim reference numeral "1700", each occurrence, should read --1710--;

Column 8, line 20, delete the text "object" and insert text --rail--.